US009576168B2

(12) United States Patent
Otis et al.

(10) Patent No.: US 9,576,168 B2
(45) Date of Patent: Feb. 21, 2017

(54) CONDITIONAL RETRIEVAL

(71) Applicant: Verily Life Sciences LLC, Mountain View, CA (US)

(72) Inventors: Brian Otis, Sunnyvale, CA (US); Daniel James Yeager, Berkely, CA (US); William Biederman, Berkeley, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 144 days.

(21) Appl. No.: 14/143,180

(22) Filed: Dec. 30, 2013

(65) Prior Publication Data

US 2015/0186701 A1    Jul. 2, 2015

(51) Int. Cl.
| | | |
|---|---|---|
| H04Q 5/22 | (2006.01) | |
| G06K 7/10 | (2006.01) | |
| A61B 5/024 | (2006.01) | |
| A61B 5/1455 | (2006.01) | |
| G06K 19/07 | (2006.01) | |
| G06K 19/077 | (2006.01) | |
| H02J 7/00 | (2006.01) | |

(52) U.S. Cl.
CPC ....... *G06K 7/10396* (2013.01); *A61B 5/02438* (2013.01); *A61B 5/1455* (2013.01); *A61B 2560/0214* (2013.01); *G06K 19/0707* (2013.01); *G06K 19/0717* (2013.01); *G06K 19/0728* (2013.01); *G06K 19/07749* (2013.01); *H02J 7/0047* (2013.01)

(58) Field of Classification Search
None
See application file for complete search history.

(56) References Cited

U.S. PATENT DOCUMENTS

| | | | |
|---|---|---|---|
| 6,850,786 B2 | 2/2005 | March | |
| 2006/0265181 A1* | 11/2006 | Stewart | 702/178 |
| 2008/0074263 A1* | 3/2008 | Rofougaran | G06K 7/0008 340/572.1 |
| 2009/0112308 A1* | 4/2009 | Kassem | 623/1.24 |
| 2010/0016704 A1 | 1/2010 | Naber et al. | |
| 2010/0113901 A1 | 5/2010 | Zhang et al. | |
| 2010/0231382 A1* | 9/2010 | Tayrani | G01D 21/00 340/539.27 |
| 2012/0086557 A1* | 4/2012 | Inatomi | 340/10.3 |

(Continued)

FOREIGN PATENT DOCUMENTS

| | | |
|---|---|---|
| KR | 1020110069113 A | 6/2011 |
| WO | 2012052765 A2 | 4/2012 |

*Primary Examiner* — Brian Zimmerman
*Assistant Examiner* — Thomas McCormack
(74) *Attorney, Agent, or Firm* — McDonnell Boehnen Hulbert & Berghoff LLP

(57) ABSTRACT

In one aspect of the present disclosure, a method is disclosed. The method involves: a reader detecting an eye-mountable device within a wireless communication range of the reader, wherein the eye-mountable device includes a transparent material having a concave mounting surface configured to be removably mounted on a corneal surface; wirelessly retrieving from the detected eye-mountable device a first set of data; using the retrieved first set of data to determine that a condition has been satisfied; and responsive to using the retrieved first set of data to determine that the condition has been satisfied, retrieving from the detected eye-mountable device a second set of data.

19 Claims, 7 Drawing Sheets

(56) References Cited

U.S. PATENT DOCUMENTS

| | | |
|---|---|---|
| 2012/0177576 A1 | 7/2012 | Hu |
| 2012/0245444 A1* | 9/2012 | Otis et al. .................... 600/345 |
| 2012/0249302 A1* | 10/2012 | Szu .................... G06K 7/10297 340/10.1 |
| 2012/0259188 A1 | 10/2012 | Besling |
| 2012/0326844 A1* | 12/2012 | Blaignan et al. ............ 340/10.1 |

* cited by examiner

CONDITIONAL RETRIEVAL

BACKGROUND

Unless otherwise indicated herein, the materials described in this section are not prior art to the claims in this application and are not admitted to be prior art by inclusion in this section.

A contact lens device can include a sensor for measuring an analyte, such as glucose, in a tear film. The sensor can be an electrochemical sensor that includes a working electrode and a counter and/or reference electrode. An electrochemical reaction involving the analyte can transfer electrons to or from the working electrode so as to generate a current related to the concentration of the analyte. In some instances, a reagent can be located proximate to the working electrode to facilitate a selective, electrochemical reaction with the analyte.

A contact lens device can also communicate sensor readings to an external reader. For example, the contact lens can include an antenna that is configured to receive radio frequency radiation from the external reader and produce a backscatter signal based on a sensor reading.

SUMMARY

In one aspect of the present disclosure, a method is disclosed. The method involves: a reader detecting an eye-mountable device within a wireless communication range of the reader, wherein the eye-mountable device includes a transparent material having a concave mounting surface configured to be removably mounted on a corneal surface; wirelessly retrieving from the detected eye-mountable device a first set of data; using the retrieved first set of data to determine that a condition has been satisfied; and responsive to using the retrieved first set of data to determine that the condition has been satisfied, retrieving from the detected eye-mountable device a second set of data.

In another aspect of the present disclosure, a reader is disclosed. The reader includes a wireless communication interface; a processor; and a computer-readable medium including instructions that, when executed by the processor, cause the reader to perform a set of functions. The set of functions includes: detecting an eye-mountable device within a wireless communication range of the reader, wherein the eye-mountable device includes a transparent material having a concave mounting surface configured to be removably mounted on a corneal surface; wirelessly retrieving, using the wireless communication interface, from the detected eye-mountable device a first set of data; using the retrieved first set to determine that a condition has been satisfied; and responsive to using the retrieved first set to determine that the condition has been satisfied, retrieving, using the wireless communication interface, from the detected eye-mountable device a second set of data.

In yet another aspect of the present disclosure, another method is disclosed. The method involves: a first reader detecting an eye-mountable device within a wireless communication range of the first reader, wherein the eye-mountable device includes a transparent material having a concave mounting surface configured to be removably mounted on a corneal surface; the first reader wirelessly retrieving from the detected eye-mountable device a first set of data; the first reader transmitting to a data collection device the retrieved first set of data; a second reader detecting the eye-mountable device within a wireless communication range of the second reader; the second reader wirelessly retrieving from the detected eye-mountable device a second set of data; and the second reader transmitting to the data collection device the retrieved second set of data.

In still another aspect of the present disclosure, disclosed are means for: detecting an eye-mountable device within a wireless communication range of a reader, wherein the eye-mountable device includes a transparent material having a concave mounting surface configured to be removably mounted on a corneal surface; wirelessly retrieving from the detected eye-mountable device a first set of data; using the retrieved first set of data to determine that a condition has been satisfied; and responsive to using the retrieved first set of data to determine that the condition has been satisfied, retrieving from the detected eye-mountable device a second set of data.

These as well as other aspects, advantages, and alternatives, will become apparent to those of ordinary skill in the art by reading the following detailed description, with reference where appropriate to the accompanying drawings.

DETAILED DESCRIPTION

I. Overview

Figure 1:
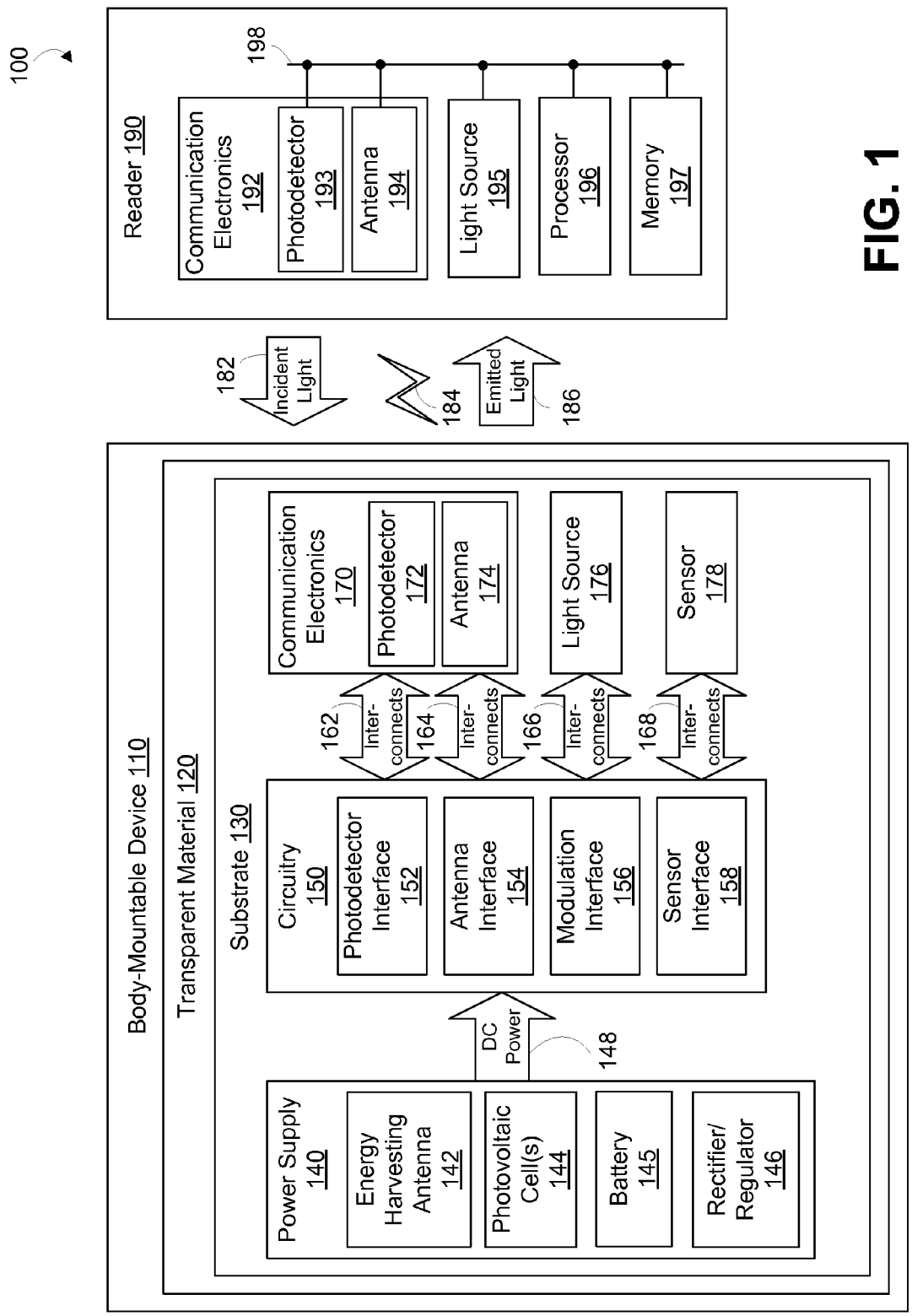
FIG. 1 is a block diagram of an example system that includes a body-mountable device and an external reader.

The following detailed description describes various features and functions of the disclosed systems and methods with reference to the accompanying figures. In the figures, similar symbols identify similar components, unless context dictates otherwise. Any reference to "a" or "an" means "at least one" and any reference to "the" means "the least one" unless otherwise specified or unless context dictates otherwise. The illustrative systems and methods described herein are not meant to be limiting. It may be readily understood by those skilled in the art that certain aspects of the disclosed systems and methods can be arranged and combined in a wide variety of different configurations, all of which are contemplated herein.

An electronic device may be utilized to obtain data and to communicate with other devices or people. The electronic device could be a body-mountable device. In an example embodiment, the body-mountable device is an eye-mountable device that can be mounted to an eye. In other examples, the body-mountable device could be mounted to a tooth, skin, or other body part. The body-mountable device can include circuitry, a sensor, and an antenna all situated on a substrate embedded in a biocompatible material. The circuitry can operate the sensor to obtain sensor data. Further, the circuitry can operate the antenna to wirelessly communicate information to and/or from an external reader. Generally, the body-mountable device may transmit information to the external reader by modulating an impedance of the antenna in a manner that is perceivable by the external reader.

In some examples, the biocompatible material is a transparent material in the form of a generally dome-shaped lens similar to a contact lens. The substrate can be embedded near the periphery of the biocompatible material to avoid interference with vision. The sensor can be arranged on the substrate to face inward, toward the corneal surface, so as to generate clinically relevant readings from near the surface of the cornea and/or from tear fluid interposed between the biocompatible material and the corneal surface. Additionally or alternatively, the sensor can be arranged on the substrate to face outward, away from the corneal surface and toward the layer of tear fluid coating the surface of the biocompatible material exposed to the atmosphere.

In some examples, the sensor is entirely embedded within the biocompatible material. For example, an electrochemical sensor that includes a working electrode and a reference electrode can be embedded in the biocompatible material and situated such that the sensor electrodes are less than 10 micrometers from the biocompatible surface configured to mount to the cornea. The sensor can generate data indicative of a concentration of an analyte that diffuses through the lens material to the sensor electrodes. In other examples, the biocompatible material includes a channel through which a fluid containing the analyte can reach the sensor.

Tear fluid contains a variety of inorganic electrolytes (e.g., $Ca^{2+}$, $Mg^{2+}$, $Cl^-$), organic components (e.g., glucose, lactate, proteins, lipids, etc.), and so on that can be used to diagnose health states. The body-mountable device can be configured to measure one or more of these analytes and can thus provide a convenient non-invasive platform useful in diagnosing and/or monitoring health states. For example, a body-mountable device can be configured to sense glucose and can be used by diabetic individuals to measure/monitor their glucose levels. In some embodiments, the sensor can be configured to measure additional or other conditions other than analyte levels (e.g., light, temperature, and current measurements).

In some instances, the body-mountable device may be configured to intermittently or periodically obtain sensor data. Additionally or alternatively, the body-mountable device may be configured to obtain sensor data in response to receiving a suitable request from the external reader. The body-mountable device may also be configured to store the obtained sensor data in a memory included in the body-mountable device, so that the body-mountable device may transmit the stored sensor data to an external reader at a later time. Additionally, the reader may generate an alert (e.g., that may be presented on a display screen) that the body-mountable device needs to be charged.

As noted above, circuitry of a body-mountable device can operate an antenna to wirelessly communicate information to and/or from an external reader. For example, when the body-mountable device is within a wireless communication range of the external reader, the circuitry can operate the antenna to receive information from the external reader. In one example, such information may include a message querying whether a body-mountable device is within a wireless communication range of the external reader ("query message"). In another example, such information may include a message requesting the body-mountable device to obtain sensor data and/or to transfer obtained sensor data to the external reader.

Likewise, provided that the external reader is within a wireless communication range of the body-mountable device, the circuitry can operate the antenna to transmit information to the external reader. In one example, such information may include a message that acknowledges receipt of a query message and/or identifies the body-mountable device ("acknowledgment message"). As such, in some instances, in response to receiving the query message from the external reader, the body-mountable device may transmit the acknowledgment message to the external reader. This may allow the external reader to detect the presence of the body-mountable device.

In another example, the information transmitted by the body-mountable device to the external reader may include sensor data stored in the body-mountable device. In some instances, the body-mountable device may transmit the stored sensor data to the external reader in response to receiving a suitable request from the external reader. Additionally or alternatively, the body-mountable device may be configured to intermittently or periodically transmit stored sensor data to the external reader.

The body-mountable device can be powered in a variety of ways. As one example, the body-mountable device may be powered by radio frequency energy harvested from an antenna included in the body-mountable device. As another example, the body-mountable device may be powered by light energy harvested by a photovoltaic cell included in the body-mountable device. As yet another example, the body-mountable device may be powered by energy stored in a battery included in the body-mountable device. In some instances, the body-mountable device may employ some combination of two or more of these options. For instance, the body-mountable device may harvest energy from the antenna and/or the photovoltaic cell, and store that harvested energy in the battery for later use.

The external reader can be configured and/or positioned such that the external reader and the body-mountable device are within a wireless communication range of each other with some regularity. For example, the external reader can be configured to be part of a pair of eyeglasses, jewelry (e.g., earrings, necklace), headband, head cover such as a hat or cap, earpiece, and/or other clothing (e.g., a scarf) or device that may be worn by a wearer of the body-mountable device. As another example, an external reader may be configured to be part of a case (e.g., a contact lens case) where the body-mountable device may be stored. In other examples, the external reader can be positioned in one or more places of a home, workspace, vehicle, or other area where the body-mountable device is likely to be present with some regularity. For instance, the external reader may be configured to be part of a desk chair at a workplace or part of a sun visor in a vehicle.

In some instances, multiple external readers may be distributed across multiple positions such as those described above, thereby creating an external reader network. With such an arrangement, as a body-mountable device moves from place to place, the body-mountable device may fall within at least one and perhaps many of the respective wireless communication ranges of the external readers with some regularity. Further, the multiple external readers may be configured to communicate with each other and/or or with a data collection device so that multiple portions of obtained sensor data retrieved by the various external readers can be aggregated together. The external readers or the data collection device can then utilize the sensor data such as by processing, presenting, displaying, storing, communicating, and/or otherwise using the data. Such data may be also encrypted using one or more known encryption techniques.

In some examples, a body-mountable device may require less power to obtain sensor data than to transmit the obtained sensor data to an external reader. In such examples, it may be beneficial for the external reader to request and/or retrieve obtained sensor data from the body-mountable device only under certain circumstances, such as when the body-mountable device has a sufficient amount of power to transmit the obtained sensor data to the external reader in a single communication session. Indeed, should the external reader attempt to retrieve the obtained sensor data when the body-mountable device does not have a sufficient amount of power to complete the transfer of such data, the body-mountable device may waste power by attempting to carry out the data transfer. This waste of power may limit the body-mountable device's ability to obtain additional sensor data.

To help address help this issue, the external reader may retrieve from the body-mountable device a first set of data that includes data other than the sensor data itself. In one example, the first set of data may include power-related data such as an indication of energy stored in a battery of the body-mountable device. Additionally or alternatively, the first set of data may include sensor metadata (i.e., data about the obtained sensor data) such as an indication of an amount of the obtained sensor data stored in the body-mountable device. The body-mountable device may then use the retrieved first set of data to determine that a condition has been satisfied. This may indicate that the body-mountable device is able to transmit the obtained sensor data to the external reader in a single communication session. In one example, the condition may be a condition that that the body-mountable device is storing a threshold amount of energy and/or a condition that the body-mountable device is not storing a threshold amount of obtained sensor data. Then, responsive to the body-mountable device determining that the condition has been satisfied, the body-mountable device may retrieve a second set of data from the body-mountable device. The second set of data may include the obtained sensor data.

Notably, if in the alternative, the body-mountable device determines that the condition has not been satisfied, the external reader may, at least temporarily, forego the process of retrieving the second set of data from the body-mountable device. This may occur, for instance, where the body-mountable device has insufficient power to transfer the obtained sensor data to the external reader. The body-mountable device may subsequently harvest and/or store additional energy such that the condition may be satisfied at a later time when the above-described process is repeated.

II. Example Systems

FIG. 1 is a block diagram of an example system 100 that includes a body-mountable device 110 and an external reader 190.

The exposed regions of the body-mountable device 110 can be made of a transparent material 120 formed to be mounted to a body. In some examples, the transparent material 120 can be contact-mounted to the body. In other examples, the transparent material 120 can be embedded in the body (e.g., surgically embedded, etc.). The transparent material 120 can have a mounting surface and a surface opposite the mounting surface. A substrate 130 may be embedded in the transparent material 120 to provide a mounting surface for a power supply 140, circuitry 150, communication electronics 170, light source 176, and a sensor 178. The communication electronics 170 may include a photo detector 172 and an antenna 174.

The power supply 140 supplies operating voltages to the circuitry 150. The circuitry 150 may provide power to and control the communication electronics 170, the light source 176, and the sensor 178. The communication electronics 170 may be operated by circuitry 150 to communicate information to and/or from the body-mountable device 110. For instance, the antenna 174 may be operated by circuitry 150 to communicate information to and/or from the body-mountable device 110.

For example, when the body-mountable device 110 is within a wireless communication range of the external reader 190, the circuitry 150 can operate the antenna 174 to receive information from the external reader 190. In one example, such information may include a query message. In another example, such information may include a message requesting the body-mountable device 110 to obtain sensor data and/or to transfer obtained sensor data to the external reader 190.

In addition, when the external reader 190 is within a wireless communication range of the body-mountable device 110, the circuitry 150 can operate the antenna 174 to transmit information to the external reader 190. In one example, such information may include an acknowledgment message. As such, in some instances, in response to receiving the query message from the external reader 190, the body-mountable device 110 may transmit the acknowledgment message to the external reader 190. This may allow the external reader 190 to detect the presence of the body-mountable device 110.

In another example, the information transmitted by the body-mountable device 110 to the external reader 190 may include sensor data stored in a memory of body-mountable device 110. In some instances, the body-mountable device 110 may transmit the stored sensor data to the external reader 190 in response to receiving a suitable request from the external reader 190. Additionally or alternatively, the body-mountable device 110 may be configured to intermittently or periodically transmit stored sensor data to the external reader 190.

The extent of the wireless communication range of the body-mountable device 110 and/or the external reader 190 may depend on various factors, including for example, the particular hardware components used to provide such wireless communication.

The light source 176 may be operated by circuitry 150 to emit light (e.g., modulated light 186 towards a photodetector 193 of the external reader 190). Additionally or alternatively, the photodetector 172 and the light source 176 can be operated by the circuitry 150 to communicate information (such as that described above in connection with the antenna 174) to and/or from the body-mountable device 110. The sensor 178 may receive power and may also be operated by circuitry 150 to provide a reading that may be communicated to from the body-mountable device 110.

In some examples where the body-mountable device 110 is an eye-mountable device configured to be contact-mounted to an eye, to facilitate contact-mounting, the transparent material 120 can have a concave surface configured to adhere ("mount") to a moistened corneal surface (e.g., by capillary forces with a tear film coating the corneal surface).

Additionally or alternatively, the body-mountable device 110 can be adhered by a vacuum force between the corneal surface and the transparent material 120 due to a concave curvature of the mounting surface of the body-mountable device 110. In this example, while mounted with the concave surface against the eye, the outward-facing surface of the transparent material 120 can have a convex curvature that is formed to not interfere with eye-lid motion while the body-mountable device 110 is mounted to the eye. For example, the transparent material 120 can be a generally dome-shaped polymeric material shaped similarly to a contact lens.

In some examples, the transparent material 120 can include one or more biocompatible materials. For example, biocompatible materials employed for use in contact lenses or other ophthalmic applications involving direct contact with a body can be used. The transparent material 120 can optionally be formed in part from such biocompatible materials or can include an outer coating with such biocompatible materials. The transparent material 120 can optionally include materials configured to moisturize a surface of the body, such as hydrogels and the like. In some embodiments where the body-mountable device is an eye-mountable device, the transparent material 120 can be shaped to provide a predetermined, vision-correcting optical power, such as can be provided by a contact lens.

The substrate 130 may include one or more surfaces suitable for mounting the power supply 140, circuitry 150, communication electronics 170, light source 176, and sensor 178. The substrate 130 can be employed both as a mounting platform for chip-based circuitry (e.g., by flip-chip mounting to connection pads) and/or as a platform for patterning conductive materials (e.g., gold, platinum, palladium, titanium, copper, aluminum, silver, metals, other conductive materials, combinations of these, etc.) to create electrodes, interconnects, connection pads, antennae, etc. In some embodiments, through hole pads may be patterned and/or drilled on to the substrate 130 to allow connections between components on more than one side of the substrate 130. For example, some components like circuitry 150 and communication electronics 170 may be disposed on one side of the substrate 130 and other components like the light source 176 and the sensor 178 may be disposed on another side of the substrate 130. In some embodiments, the substrate 130 may be a multilayer substrate (e.g., printed circuit board) that allows connections between components included in the body-mountable device 110 in several layers between multiple sides of the substrate 130. In some embodiments, substantially transparent conductive materials (e.g., indium tin oxide) can be patterned on the substrate 130 to form circuitry 150, electrodes, etc. For example, the antenna 174 can be formed by forming a pattern of gold or another conductive material on the substrate 130 by deposition, photolithography, electroplating, etc. Similarly, interconnects 162, 164, 166, 168 between the circuitry 150 and the photodetector 172, antenna 174 light source 176, and sensor 178 respectively, can be formed by depositing suitable patterns of conductive materials on the substrate 130. In some embodiments, interconnects 168 may be similarly formed to connect circuitry 150 with sensor 178.

A combination of microfabrication techniques including, without limitation, the use of photoresists, masks, deposition techniques, and/or plating techniques can be employed to pattern materials on the substrate 130. In some examples, the substrate 130 can be a rigid material, such as polyethylene terephthalate ("PET") or a flexible material, such as polyimide or organic materials configured to structurally support the circuitry 150 and/or chip-based electronics within the transparent material 120. The body-mountable device 110 can alternatively include a group of unconnected substrates rather than a single substrate. For example, the circuitry 150 can be mounted to one substrate, while the light source 172 is mounted to another substrate and the two can be electrically connected via interconnects 162.

In some embodiments where the body-mountable device 110 is an eye-mountable device, the substrate 130 (and other components included in the body-mountable device 110) can be positioned away from the center of the body-mountable device 110 and thereby avoid interference with light transmission to the central, light-sensitive region of the eye (e.g., avoid field of view of the eye). For example, where the body-mountable device 110 is generally dome-shaped, the substrate 130 can be embedded around the periphery (e.g., near the outer circumference) of the dome. In some embodiments, however, the substrate 130 can be positioned in or near the central region of the body-mountable device 110. For example, the body-mountable device 110 can be a tooth-mounted device, and the substrate 130 can be embedded in any location inside the transparent material 120. Additionally or alternatively, the substrate 130 (and other components included in the body-mountable device 110) can be substantially transparent to incoming visible light to mitigate interference with light transmission to the body. For example, the body-mountable device 110 can be a skin-mounted device, and the substrate 130 can be substantially transparent to allow sunlight to reach the skin.

In some embodiments, the substrate 130 can be shaped as a flattened ring with a radial width dimension sufficient to provide a mounting platform for embedded electronics components. The substrate 130 can have a thickness sufficiently small to allow the substrate 130 to be embedded in the transparent material 120 without influencing a shape of the body-mountable device 110. The substrate 130 can have a thickness sufficiently large to provide structural stability suitable for supporting electronics mounted thereon. For example, substrate 130 can be shaped as a ring with a diameter of about 10 millimeters, a radial width of about 1 millimeter (e.g., an outer radius 1 millimeter larger than an inner radius), and a thickness of about 50 micrometers. However, the diameter, radial width and thickness values are provided for explanatory purposes only. In some embodiments, the dimensions of the substrate 130 can be selected according to the size and/or shape of the body-mountable device 110. The substrate 130 can optionally be aligned with a curvature of a surface of the body-mountable device 110.

The power supply 140 may be configured to harvest and/or store energy to power the circuitry 150, communication electronics 170, light source 176, and sensor 178. For example, a radio-frequency energy-harvesting antenna 142 can capture energy from incident radio frequency radiation. Additionally or alternatively, photovoltaic cell(s) 144 (e.g., solar cells) can capture energy from incoming ultraviolet, infrared, visible, and/or invisible radiation. In some embodiments, the incident radio frequency radiation and/or incoming radiation may be ambient radiation in surroundings of the body-mountable device 110. Additionally or alternatively, the incident radio frequency radiation and/or incoming radiation may be from the external reader 190. Furthermore, an inertial power scavenging system can be included to capture energy from ambient vibrations. The energy harvesting antenna 142 can optionally be a dual-purpose antenna that is also used to communicate information from/to the external reader 190. That is, the functions of the antenna 174 and the energy harvesting antenna 142 can be accomplished with a same physical antenna.

The power supply 140 may also include a battery 145 for storing energy. The battery 145 may take a variety of forms. For example, the battery 145 may take the form of a rechargeable battery such as a nickel-cadmium (NiCd), nickel-metal hydride (NiMH), or lithium ion (Li-ion) battery. In some instances, the battery 145 may be configured such that it may be charged by an inductive or wireless charging process (e.g., when in close proximity to a reader configured to charge the battery in this manner). Additionally or alternatively, the battery may be configured to store energy harvested via the energy harvesting antenna 142 and/or the photovoltaic cells 144.

In one example, a rectifier/regulator 146 can be used to condition harvested and/or stored energy to a stable DC supply voltage 148 that is supplied to circuitry 150. For example, the energy harvesting antenna 142 can receive incident radio frequency radiation. Varying electrical signals on the leads of the energy harvesting antenna 142 are output to the rectifier/regulator 146. The rectifier/regulator 146 rectifies the varying electrical signals to a DC voltage and regulates the rectified DC voltage to a level suitable for operating circuitry 150. Additionally or alternatively, output voltage from the photovoltaic cell(s) 144 and/or the battery 145 can be regulated to a level suitable for operating the circuitry 150. The rectifier/regulator 146 can include one or more energy storage devices to mitigate high frequency variations in the energy harvesting antenna 142 and/or photovoltaic cell(s) 144. For example, one or more energy storage devices (e.g., capacitors, inductors, etc.) can be connected with the outputs of the rectifier/regulator 146 to regulate the DC supply voltage 148 and/or configured to function as a low-pass filter.

The circuitry 150 is activated when the DC supply voltage 148 is provided to the circuitry 150. The logic in the circuitry 150 may operate the communication electronics 170 to interact with external reader 190. The logic in circuitry 150 may also operates sensor 178 to obtain sensor data. In addition, the logic in the circuitry 150 may operate the light source 176.

In one example, the circuitry 150 may operate the light source 176 such that the body-mountable device 110 may communicate with the reader 190. In particular, the circuitry 150 can be configured to receive modulation instructions and control light source 176 to provide modulated emitted light 186 towards the photodetector 196 based on the modulation instructions. Additionally or alternatively, the circuitry 150 may be configured to receive the modulation instructions through interaction with the photodetector 172, antenna 174 and/or sensor 178. In one example, the circuitry 150 includes a photodetector interface 152 that is configured to operate photodetector 172 that may be included in the communication electronics 170. The photodetector 172 can be, for example, an active pixel sensor (APS), charge-coupled device (CCD), photodiode, photoresistor, phototransistor, camera, or any other sensor of light configured to provide a signal through interconnects 162 indicative of incident light 182 on the body-mountable device 110. The incident light 182 may be visible light or invisible light (ultraviolet, infrared, etc.). The incident light 182 detected by the photodetector 172 may be indicative of a message, modulation instructions for the light source 176 included in the body-mountable device 110, or other data. For example, the circuitry 150 may modulate light emitted by light source 176 based on the message. In other examples, the circuitry 150 may control components included in the substrate 130 based on the message.

In some instances, the circuitry 150 may include an antenna interface 154 that is configured to operate antenna 174 included in the communication electronics 170 to send and/or receive information via antenna 174. The antenna interface 154 can optionally include one or more oscillators, mixers, frequency injectors, etc. to modulate and/or demodulate information on a carrier frequency to be transmitted and/or received by the antenna 174. In some examples, the body-mountable device 110 is configured to indicate an output from sensor 178 by modulating an impedance of the antenna 174 in a manner that is perceivable by the external reader 190. For example, the antenna interface 154 can cause variations in the amplitude, phase, and/or frequency of radio frequency radiation (RF radiation) 184 from the antenna 174, and such variations can be detected by the reader 190. RF radiation 184 may also include radiation from the reader 190 to the antenna 174. In some examples, the body-mountable device 110 is configured to receive RF radiation 184 from the external reader 190 that is indicative of a message (e.g., a message requesting obtained sensor data), the modulation instructions for the light source 176, or other data. For example, circuitry 150 may modulate light emitted by light source 176 based on the message. In other examples, the circuitry 150 may control components included in the substrate 130 based on the message. The antenna interface 154 can be connected to antenna 174 via interconnects 164.

The circuitry 150 can also include a modulation interface 156 for modulating light emitted by light source 176. The light emitted by light source 176 could be visible light or invisible light (ultraviolet, infrared, etc.). The circuitry 150 can include logic elements and/or controllers implemented in an integrated circuit to form the modulation interface 156. For example, the modulation interface 156 can modify an aspect of the emitted light 186 by light source 176 like wavelength (i.e., color), brightness, intensity, or duration of the emitted light to provide modulated light. The light source 176 may take a variety of forms, including for example a light emitting diode (LED), vertical cavity surface emitting laser (VCSEL), organic light emitting diode (OLED), liquid crystal display (LCD), microelectromechanical system (MEMS), or any other device configured to selectively transmit, reflect, and/or emit light according to information from the modulation interface 156 via the interconnects 166 to provide the modulated emitted light 186. Also, the light source 176 may be constructed and/or arranged on the substrate 130 in a particular manner so that the light source 176 can emit light in a particular direction (and/or at a particular angle).

In some examples, the modulation interface 156 can include one or more data lines providing programming information to separately programmed pixels in the light source 176. In some examples, the light source 176 may also include one or more optical elements to direct the emitted light 186 through the surface opposite the mounting surface of the transparent material 120. In examples where the body-mountable device 110 is an eye-mountable device, the light source 176 disposed on the substrate 130 can be configured to emit light through the convex surface (e.g., surface opposite the mounting surface) of the transparent material 120 and away from a corneal surface of an eye when the concave surface (e.g., the mounting surface) of the transparent material 120 is mounted on the corneal surface of the eye.

The circuitry 150 may include a sensor interface 158 for operating the sensor 178. The sensor 178 can be, for example, a bio-sensor configured to measure an analyte in a tear film. For example, the sensor 178 can be a glucose sensor configured to provide a reading relating to glucose level in the tear film. In some examples, the sensor 178 may measure other biological information like blood pressure, temperature, heart rate or psychological state of the user of the body-mountable device 110. For example, the sensor 178 can be configured to measure a frequency of eye-blinks to determine the psychological state of the user. In another example, the sensor 178 can be configured to measure the concentration of an analyte in saliva (e.g., where the body-mountable device 110 is a tooth-mounted device). In some examples, the sensor 178 may measure aspects of a surrounding environment of the user. For example, the sensor 178 may measure the ambient light intensity or humidity of the surrounding environment. In some examples, the received modulation instructions may be based on the reading of the sensor. For example, the circuitry 150 may be configured to modulate the intensity of the emitted light 186 by the light source 176 according to the intensity of ambient light indicated by the reading of the sensor 178. In other examples, the modulated emitted light 186 may be indicative of the reading of the sensor (e.g., red color may indicate high glucose level, blue color may indicate low glucose level, etc.).

In some instances, the body-mountable device 110 may be configured to intermittently or periodically obtain sensor data. In such instances, the external reader 190 may transmit to the body-mountable device 110 instructions related to the operation of the sensor 178. For example, the external reader 190 may instruct the body-mountable device 110 to use the sensor 178 to obtain sensor readings according to a particular schedule (e.g., at a particular frequency). Additionally or alternatively, the body-mountable device 110 may be configured to obtain sensor data in response to receiving a suitable request from the external reader 190. The body-mountable device 110 may also be configured to store the obtained sensor data in a memory included in the body-mountable device 110, so that the body-mountable device may transmit the stored sensor data to an external reader 190 at a later time.

The circuitry 150 is connected to the communication electronics 170 via interconnects 162 and 164. For example, where the circuitry 150 includes logic elements implemented in an integrated circuit to form the photodetector 172 and/or the antenna 174, a patterned conductive material (e.g., gold, platinum, palladium, titanium, copper, aluminum, silver, metals, combinations of these, etc.) can connect a terminal on the chip to communication electronics 170. Similarly, the circuitry 150 can be connected to the light source 176 via interconnects 166, and the circuitry 150 can be connected to the sensor 178 via interconnects 168.

It is noted that the block diagram shown in FIG. 1 is described in connection with functional modules for convenience in description. However, embodiments of the body-mountable device 110 can be arranged with one or more of the functional modules ("subsystems") implemented in a single chip, integrated circuit, and/or physical component. For example, while the rectifier/regulator 146 is illustrated in the power supply block 140, the rectifier/regulator 146 can be implemented in a chip that also includes the logic elements of circuitry 150 and/or other features of the embedded electronics in the body-mountable device 110. Thus, the DC supply voltage 148 that is provided to the circuitry 150 from the power supply 140 can be a supply voltage that is provided to components on a chip by rectifier and/or regulator 146 components located on a same chip. That is, the functional blocks in FIG. 1 shown as the power supply block 140 and circuitry block 150 need not be implemented as physically separated modules. Additionally or alternatively, the energy harvesting antenna 142 and the antenna 174 can be implemented with the same physical antenna. For example, a loop antenna can both harvest incident radiation for power generation and communicate information via backscatter radiation.

Moreover, one or more of the functional modules described in FIG. 1 can be implemented by separately packaged chips electrically connected to one another. In another example, one or more of these functional modules may be implemented in the form of a processor and a memory such as a non-transitory computer-readable medium including instructions that, when executed by the processor, cause performance of one or more of the functions described in the examples included in the present disclosure. As such, the body-mountable device 110 and/or the circuitry 150 may be configured to perform one or more of such functions. Note that the memory may also be used for other purposes including, for example, storing obtained sensor data.

The external reader 190 can be a smart phone, digital assistant, head-mountable device (e.g., eye glasses with computing capability), or other computing device with wireless connectivity sufficient to provide the RF radiation 184 and/or the incident light 182. The external reader 190 can also be implemented as an antenna module and/or light source module that can be plugged in to a computing device, such as in an example where the RF radiation 184 operates at carrier frequencies not commonly employed in computing devices, or in an example where the computing device does not include a light source. The external reader 190 can also be configured to receive the emitted light 186 from the body-mountable device 110 via the reader photodetector 196.

The external reader 190 can be configured and/or positioned such that the external reader 190 and the body-mountable device 110 are within wireless communication ranges of each other with some regularity. For example, the external reader 190 can be configured to be part of a pair of eyeglasses, jewelry (e.g., earrings, necklace), headband, head cover such as a hat or cap, earpiece, and/or other clothing (e.g., a scarf) or device that may be worn by a wearer of the body-mountable device 110. As another example, an external reader 190 may be configured to be part of a case (e.g., a contact lens case) where the body-mountable 110 device may be stored. In other examples, the external reader 190 can be positioned in one or more places of a home, workspace, vehicle, or other area where the body-mountable device 110 is likely to be present with some regularity. For instance, the external reader 190 may be configured to be part of a desk chair at a workplace or part of a sun visor in a vehicle.

As shown in FIG. 1, the external reader 190 may include communication electronics 192, a light source 195, a processor 196, and a memory 197, each of which may be connected to each other by a system bus or other connection mechanism 198. The communications electronics 192 may allow the external reader 190 to communicate information to and/or from the body-mountable device 110 or another device (e.g., another external reader or a data collection device).

In an example where the body-mountable device 110 includes the photodetector 172, the external reader 190 may include the light source 195 configured to provide modulated incident light 182 to the body-mountable device 110. For example, the modulated incident light 182 may indicate the received modulation instructions to the circuitry 150 such that the circuitry 150 modulates the emitted light 186 based on the received modulation instructions. In another example, the modulated incident light 182 may include instructions to the body-mountable device 110 to obtain a reading of the sensor 178. Thus, in this example, the circuitry 150 may be configured to modulate the emitted light 186 to provide modulated light indicative of the reading of the sensor 178.

In some examples, the communications electronics 192 can include a photodetector 196 to receive the modulated emitted light 186 and determine the reading of the sensor 178 based on the modulated emitted light 186. In some examples, the modulated incident light 182 may be indicative of a status of the external reader 190 or components included in the external reader 190. In other examples, the modulated emitted light 186 may be indicative of a status of the body-mountable device 110 or a status of components included in the body-mountable device 110. For example, the status of photovoltaic cell(s) 144 may be indicated by the modulated emitted light 186. In some examples, the external reader 190 can provide light to the photovoltaic cell(s) 144 included in the body-mountable device 110 that are configured to harvest the light to provide power to the body-mountable device 110.

In an example where the body-mountable device 110 includes an antenna 174, the external reader 190 may include the antenna 194 configured to send and/or receive information from the body-mountable device 110 via the RF radiation 184. For example, the antenna 174 may be configured to send a query message or a message pertaining to the reading of the sensor 178 through RF radiation 184. Thus, the RF radiation 184 may be received by the antenna 194 and the reading of the sensor 178 may be determined by the external reader 190 based on the RF radiation 184. In some examples, the antenna 194 may transmit information to the body-mountable device 110 via the RF radiation 184. In some examples, the external reader 190 may provide the RF radiation 184 to the energy harvesting antenna 142 included in the body-mountable device 110 that is configured to harvest the RF radiation 184 to provide power to the body-mountable device 110.

As noted above, the communication electronics 192 may allow the external reader 190 to communicate information to and/or from other devices such as another external reader or a data collection device. In one example, the communication electronics 192 may take the form of a wired or wireless interface and may allow the external reader 190 to communicate with another device such as the body-mountable device 110, another reader 190, or a data collection device according to one or more standards or protocols; e.g., an RFID standard (e.g., EPC Gen 2), a Bluetooth standard, an IEEE 802.11 protocol ("Wi-Fi"), an IEEE 802.15 protocol ("Zigbee"), a Local Area Network (LAN) protocol, a Wireless Wide Area Network (WWAN) protocol such as but not limited to a 2G protocol (e.g., CDMA, TDMA, GSM), a 3G protocol (e.g., CDMA-2000, UMTS), a 4G protocol (e.g., LTE, WiMAX), a wired protocol (e.g., USB, a wired IEEE 802 protocol, RS-232, DTMF, dial pulse). Many other examples of standard(s), protocol(s), and combination(s) of the same can be used as well. Notably, in some instances, the standard or protocol used may allow the external reader 190 may communicate with multiple different body-mountable devices 110 within simultaneously.

The processor 196 may be configured to control communications electronics 192 (including the photodetector 193 and the antenna 194) and the light source 195. The memory 197 may take the form of a non-transitory computer-readable medium including instructions that, when executed by the processor 196, cause performance of one or more of the functions described in the examples included in the present disclosure. As such, the external reader 190 may be configured to perform one or more of such functions.

In some embodiments, the system 100 can operate to intermittently supply energy to the body-mountable device 110 for the power supply 140. For example, incident light 182 and/or RF radiation 184 can be supplied to power the body-mountable device 110 long enough to obtain a reading by the sensor 178 and wirelessly communicate the reading via emitted light 186 and/or RF radiation 184 to the external reader 190. In such an example, the incident light 182 and/or the RF radiation 184 can be considered an interrogation signal from the external reader 190 to the body-mountable device 110 to request a reading. By periodically interrogating the body-mountable device 110 (e.g., by supplying the incident light 182 and/or RF radiation 184 to temporarily turn the device on), the external reader 190 can accumulate a series of readings without continuously powering the body-mountable device 110. In another example, the body-mountable device 110 may be configured to use stored energy in the battery 145 to intermittently obtain sensor data. The external reader 190 may then conditionally retrieve such readings from the body-mountable device 110 as described in greater detail below.

The external reader 190 can be configured and/or positioned such that the external reader 190 and the body-mountable device 110 are within a wireless communication range of each other with some regularity. To this end, multiple external readers 190 may be distributed across multiple locations to provide an external reader network. With such an arrangement, as the body-mountable device 110 moves from place to place, the body-mountable device 110 may fall within at least one and perhaps many of the respective wireless communication ranges of the external readers 190 with some regularity. Further, the multiple external readers 190 may be configured to communicate with each other and/or with a data collection device so that multiple portions of obtained sensor data (for a particular body-mountable device) retrieved by the various external readers 190 can be aggregated together.

Figure 3:
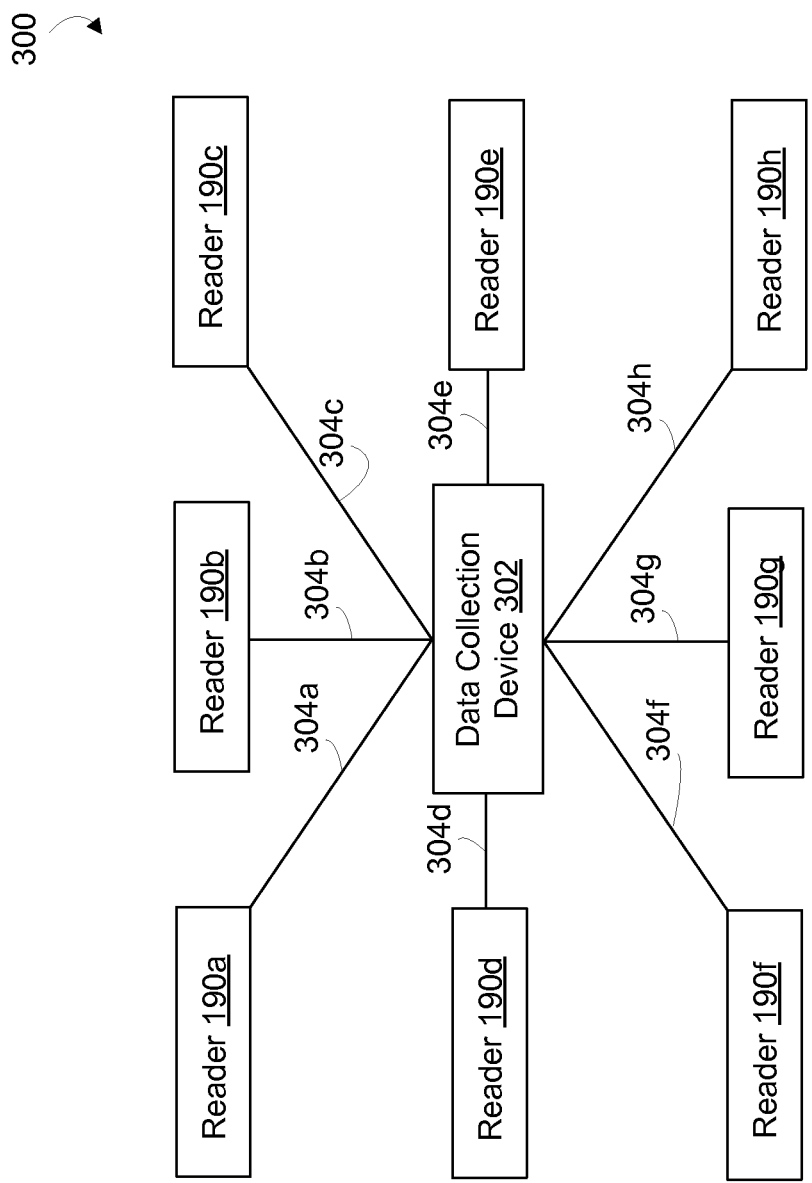
FIG. 3 is a block diagram of an example system that includes multiple external readers and a data collection device.

FIG. 3 shown an example system 300 that includes a network of eight external readers 190a-190h and a data collection device 302. Like the external reader 190 described above, the data collection device 302 may include communications electronics, a processor, and a non-transitory computer-readable medium including instructions that, when executed by the processor, cause performance of one or more of the functions described in the examples included in the present disclosure. As shown in FIG. 3, the external readers 190a-h may communicate with the data collection device 302 via respective communication paths 304a-e. The external readers 190a-h or the data collection device 302 can then utilize the sensor data such as by processing, presenting, displaying, storing, communicating, and/or otherwise using the data.

As described above, the external readers 190a-h may attempt to detect the presence of a body-mountable device 110 in their respective wireless communication ranges by broadcasting a query message. The body-mountable device 110 may be configured such that, in response to receiving the query message, the body-mountable device transmits an acknowledge message back to the external reader 190. The acknowledgement message allows the external reader to determine the presence of and/or identify the body-mountable device 110. In some instances, the external reader 190 may be configured to intermittently or periodically broadcast a query message. In other instances, the external reader 190 may transmit such a message in response to a request received from a user via a user interface.

Figure 2A:
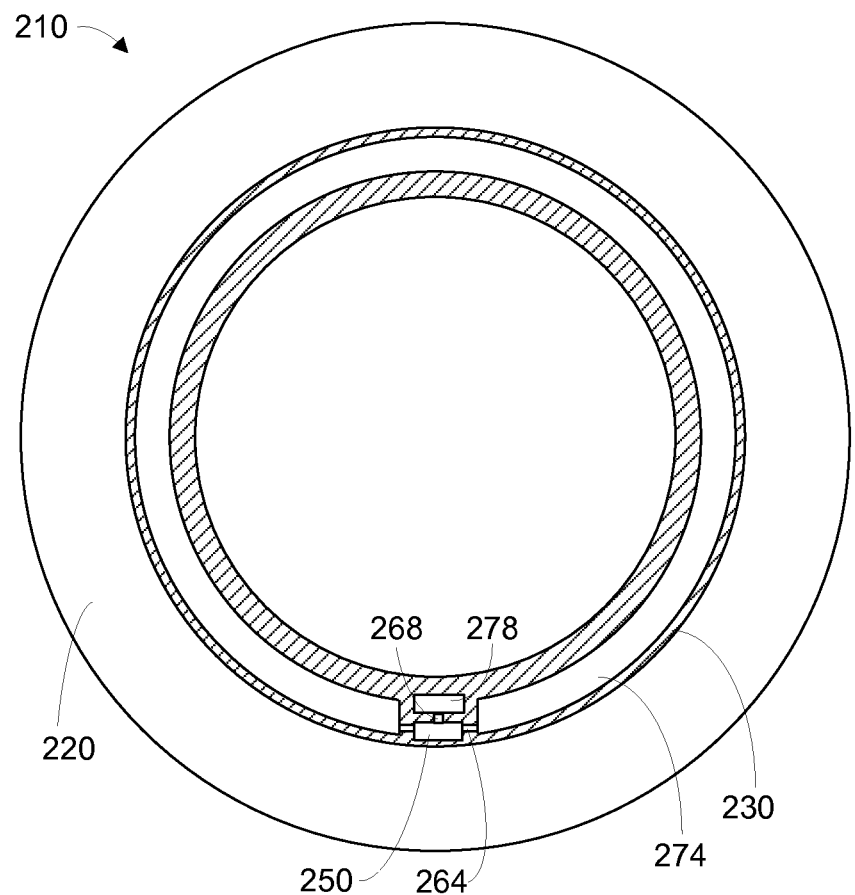
FIG. 2A is a bottom view of an example eye-mountable device.
Figure 2B:
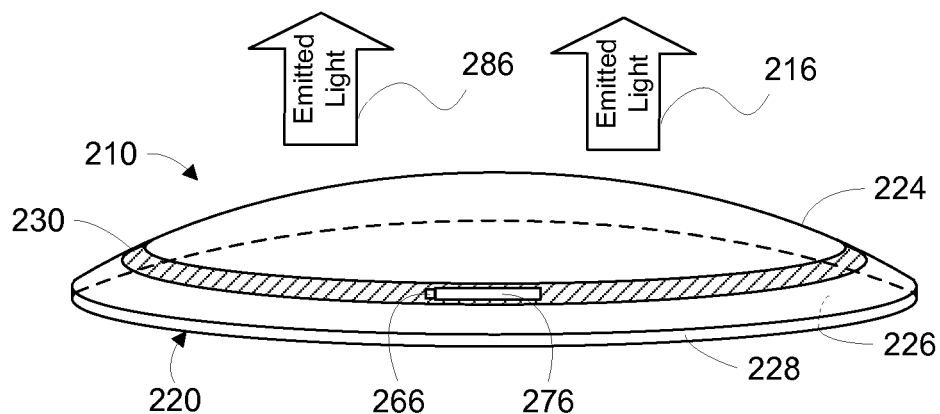
FIG. 2B is a side view of the example eye-mountable device shown in FIG. 2A.

FIG. 2A is a bottom view of an example eye-mountable device 210. FIG. 2B is a side view of the example eye-mountable device 210 shown in FIG. 2A. It is noted that the relative dimensions in FIGS. 2A and 2B are not necessarily to scale, but have been rendered for purposes of explanation only in describing the arrangement of the example eye-mountable device 210. The eye-mountable device 210 can be formed of a generally dome-shaped transparent material 220. The transparent material 220 can allow incident light (e.g., field of view of the eye) to be transmitted to the eye while the eye-mountable device 210 is mounted to the eye. In some examples, the transparent material 220 can be a biocompatible polymeric material similar to those employed to form vision correction and/or cosmetic contact lenses in optometry, such as polyethylene terephthalate (PET), polymethyl methacrylate (PMMA), polyhydroxyethylmethacrylate (polyHEMA), silicone hydrogels, combinations of these, etc. The transparent material 220 can be formed with one side having a concave surface 226 (e.g., "mounting surface", bottom-view surface shown in FIG. 2A, etc.) suitable to fit over a corneal surface of the eye. The opposite side of the dome can have a convex surface 224 ("surface opposite the mounting surface") that does not interfere with eyelid motion while the eye-mountable device 210 is mounted to the eye. A circular outer side edge 228 can connect the concave surface 226 and the convex surface 224.

The eye-mountable device 210 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 210 can be selected according to the size and/or shape of the corneal surface of the wearer's eye.

The transparent material 220 can be formed with a dome or curved shape in a variety of ways. For example, techniques similar to those employed to form vision-correction contact lenses, such as heat molding, injection molding, spin casting, etc. can be employed to form the transparent material 220. When the eye-mountable device 210 is mounted to an eye, the convex surface 224 faces outward to an ambient environment while the concave surface 226 faces inward, toward the corneal surface. The convex surface 224 can therefore be considered an outer, top surface of the eye-mountable device 210 whereas the concave surface 226 can be considered an inner, bottom surface. The "bottom" view shown in FIG. 2A is facing the concave surface 226.

A substrate 230 is embedded in the transparent material 220. In some examples, the substrate 230 can be embedded to be proximate an outer periphery of the transparent material 220, away from a central region of the eye-mountable device 210. Thus, in this example, the substrate 230 does not interfere with vision because it is too close to the eye to be in focus and is positioned away from the central region where ambient light is transmitted to light-sensing portions of the eye. In some examples, the substrate 230 can be formed of a transparent material to further mitigate effects on visual perception.

The substrate 230 can be shaped as a flat, circular ring (e.g., a disk with a centered hole). The flat surface of the substrate 230 (e.g., along the radial width) is a platform for mounting electronics such as chips (e.g., via flip-chip mounting) and for patterning conductive materials (e.g., via microfabrication techniques such as photolithography, deposition, plating, etc.) to form electrodes, antenna(e), and/or interconnections. In some examples, the substrate 230 and the transparent material 220 can be substantially cylindrically symmetric about a common central axis. The substrate 230 can have, for example, a diameter of about 10 millimeters, a radial width of about 1 millimeter (e.g., an outer radius 1 millimeter greater than an inner radius), and a thickness of about 50 micrometer. However, these dimensions are provided for example purposes only, and in no way limit the present disclosure. The substrate 230 can be implemented in a variety of different form factors, similar to the discussion of the substrate 130 in connection with FIG. 1 above.

Circuitry 250, a loop antenna 274 and a sensor 278 are disposed on a side of the substrate 230 that is facing the concave surface 226 ("bottom side") of the transparent material 220 as shown in FIG. 2A. A light source 276 is disposed on an opposite side of the substrate 230 that is facing the convex surface 224 of the transparent material 220 ("top side") as shown in FIG. 2B. However, in some embodiments, circuitry 250, the loop antenna 274, the light source 276 and/or the sensor 278 may be disposed on any side of the substrate 230. For example, in some embodiments, the circuitry 250 may be disposed in the opposite side ("top side") of the substrate 230 that is facing the convex surface 224 of the transparent material 220. In one example, the light source 276 may be disposed on the side of the substrate 230 that is facing the concave surface 226 ("bottom side"). In that case, the substrate 230 may include a hole through which light emitted by the light source 276 can reach the convex surface 224 and propagate away from the corneal surface. In some examples, one or more components disposed on the substrate 230 may be disposed on a side of the substrate 230 that is facing the circular outer side edge 228 of the transparent material 220.

In some embodiments not illustrated in FIGS. 2A-2B, the substrate 230 may include multiple layers for interconnects and other conductive material connected to components disposed on the substrate 230. Other configurations of the substrate 230 are contemplated herein and may be obvious to those of ordinary skill in the art. For example, one of the multiple layers may be utilized as "a ground plane" for the components to connect to a ground voltage.

The circuitry 250 may include logic elements (e.g., in the form of a chip, or a processor and a non-transitory computer-readable medium) configured to operate the loop antenna 274, the light source 276 and the sensor 278. The circuitry 250 is electrically coupled to the loop antenna 274 and the sensor 278, respectively, by interconnects 264 and 268. Interconnects 266 electrically connect the circuitry 250 with the light source 276 through the substrate 230. For example, interconnects 266 may be arranged in a through hole connecting the side of the substrate 230 that is facing the concave surface 226 ("bottom side") of the transparent material 220 to the opposite side of the substrate 230 that is facing the convex surface 224 ("top side") of the transparent material 220. The interconnects 264, 266, 268, and the loop antenna 274 can be formed from conductive materials patterned on the substrate 230 by a process for patterning such materials, such as deposition, photolithography, etc. The conductive materials patterned on the substrate 230 can be, for example, gold, platinum, palladium, titanium, carbon, aluminum, copper, silver, silver-chloride, conductors formed from noble materials, metals, combinations of these, etc. The circuitry 250 can be configured to receive modulation instructions and configured to modulate emitted light 286 from the light source 276 towards a photodetector of a reader based on the received modulation instructions.

The loop antenna 274 can be a layer of conductive material patterned along a flat surface of the substrate to form a flat conductive ring. In some instances, the loop antenna 274 can be formed without making a complete loop. For instance, the loop antenna 274 can have a cutout to allow room for the circuitry 250 and the sensor 278, as illustrated in FIG. 2A. However, the loop antenna 274 can also be arranged as a continuous strip of conductive material that wraps entirely around the flat surface of the substrate 230 one or more times. For example, a strip of conductive material with multiple windings can be patterned on a side of the substrate 230 opposite the circuitry 250 and sensor 278. Thus, in this example, interconnects 264 between the ends of such a wound antenna (e.g., antenna leads) can then be passed through the substrate 230 to the circuitry 250 similarly to interconnects 266 in FIG. 2B.

The light source 276 may take a variety of forms, including for example a light emitting diode (LED), vertical cavity surface emitting laser (VCSEL), organic light emitting diode (OLED), liquid crystal display (LCD), microelectromechanical system (MEMS), or any other device configured to selectively transmit, reflect, and/or emit light according to received modulation instructions by the circuitry 250 via the interconnects 266 to provide the modulated emitted light 286. The light source 276 may be configured to emit light having any of a variety of aspects (wavelength, etc.) as described above. Also, the light source 276 may be constructed and/or arranged on the substrate 230 in a particular manner so that the light source 276 can emit light in a particular direction (and/or at a particular angle). Operation of the light source 276 is similar to light source 176 discussed in FIG. 1. The light source 276 is configured to provide the emitted light 286 through the convex surface 224 and away from the corneal surface.

Although illustrated in FIG. 2B that interconnects 266 are connected to one end of the light source 276, some embodiments may include the interconnects 266 connected to any other part of the light source 276. For example, the interconnects 266 may be arranged underneath the light source 276 so that they are not viewable from the "top" side of the eye-mountable device 210 (the side facing the convex surface 224).

The light source 276 may be configured in a rectangular, triangular, circular and/or any shape that is compatible with the flat surface of the substrate 230. For example, the light source 276 may have a loop shape similar to the loop antenna 274. The light source 276 may be configured to provide the emitted light 286 based on the received modulation instructions by the circuitry 250. For example, the emitted light 286 may be indicative of a status of the eye-mountable device 210 or a status of components included in the eye-mountable device 210. For example, the emitted light 286 may be a blinking light that indicates insufficient power being provided to the eye-mountable device 210.

The sensor 278 can be disposed on the substrate 230 and configured to provide a reading to circuitry 250 via interconnects 268. For example, the received modulation instructions may be indicative of the reading of the sensor 278. In some examples, the received modulation instructions may be a response to radio frequency radiation received by the loop antenna 274 indicative of obtaining the reading from the sensor 278.

Figure 2D:
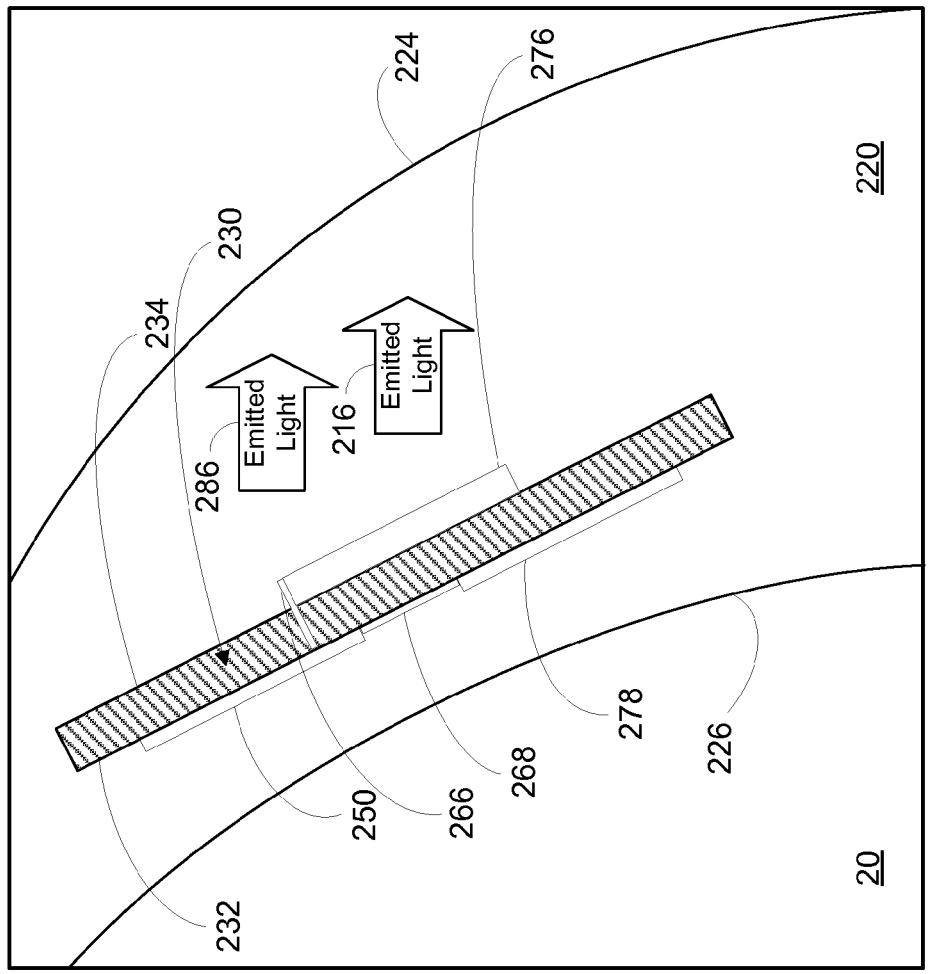
FIG. 2D is a close-in side cross-section view enhanced to show the substrate embedded in the transparent material, the light source, and the emitted light in the example eye-mountable device when mounted as shown in FIG. 2C.
Figure 2C:
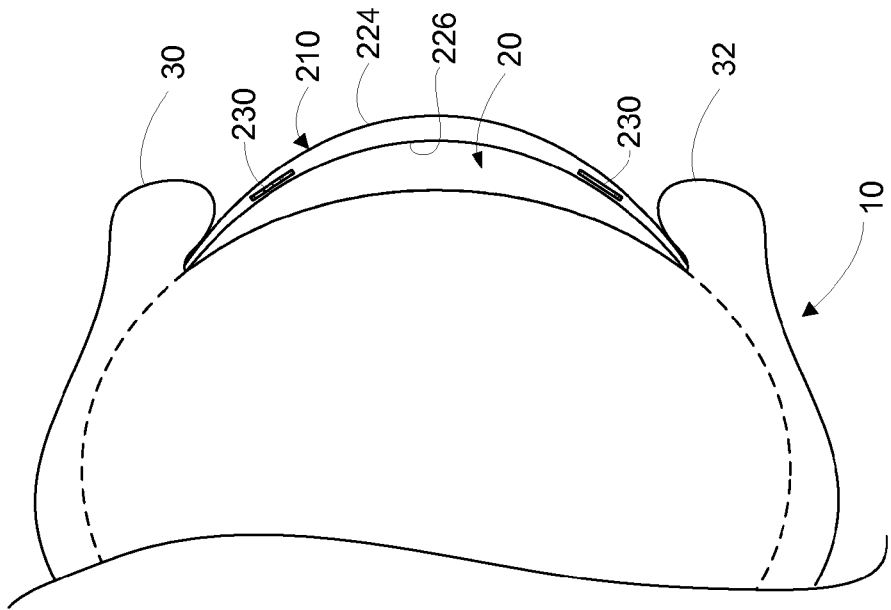
FIG. 2C is a side cross-section view of the example eye-mountable device shown in FIGS. 2A and 2B while mounted to a corneal surface of an eye.

FIG. 2C is a side cross-section view of the example eye-mountable device shown in FIGS. 2A and 2B while mounted to a corneal surface 20 of an eye 10. FIG. 2D is a close-in side cross-section view enhanced to show the substrate 230 embedded in the transparent material 220, the light source 276, and the emitted light 216, 286 in the example eye-mountable device 210 when mounted as shown in FIG. 2C. It is noted that relative dimensions in FIGS. 2C and 2D are not necessarily to scale, but have been rendered for purposes of explanation only in describing the arrangement of the example eye-mountable device 210. Some aspects are exaggerated to allow for illustration and facilitate explanation. It is further noted that the orientation of the substrate 230 embedded in the transparent material 220 is not necessarily as shown in FIG. 2D. In some embodiments, the substrate 230 may be oriented at any angle such that an outward-facing flat mounting surface 234 of the substrate 230 is facing the convex surface 224 of the transparent material 220 and an inward-facing flat mounting surface 232 of the substrate 230 is facing the concave surface 226 of the transparent material 220.

The eye 10 includes a corneal surface 20 that is covered by bringing an upper eyelid 30 and a lower eyelid 32 together over eye 10. Ambient light is received by the eye 10 through the corneal surface 20, where the ambient light is optically directed to light sensing elements of the eye 10 (e.g., rods and cones, etc.) to stimulate visual perception. As illustrated in FIG. 2C, the concave surface 226 is configured to be removably mounted to the corneal surface 20. Additionally, the convex surface 224 is compatible with motion of the eyelids 30 and 32.

As illustrated in FIG. 2D, the emitted light 216, 286 from the light source 276 is directed away from the corneal surface 20 and through the convex surface 224 when the concave surface 226 is mounted on the corneal surface 20. For example, the light source 276 can be disposed on the outward-facing flat mounting surface 234 of the substrate 230 to allow the emitted light 216, 286 to travel through the convex surface 224. In the example, interconnects 266 connect the circuitry 250, disposed on the inward-facing flat mounting surface 232 of the substrate 230, to the light source 276 through the substrate 230.

As shown in the cross-sectional views in FIGS. 2C and 2D, the substrate 230 can be inclined such that the flat mounting surfaces 232 and 234 are approximately parallel to an adjacent portion of the concave surface 226. However, in some embodiments, the substrate 230 can be oriented at any angle such that the outward-facing mounting surface 234 is facing the convex surface 224. As described above, the substrate 230 can be a flattened ring with the inward-facing surface 232 (closer to the concave surface 226 of the transparent material 220) and the outward-facing surface 234 (closer to the convex surface 224). The substrate 230 can have electronic components and/or patterned conductive materials mounted to either or both mounting surfaces 232, 234 or through the substrate 230 to connect components from one surface to another.

III. Example Operations

Figure 4:
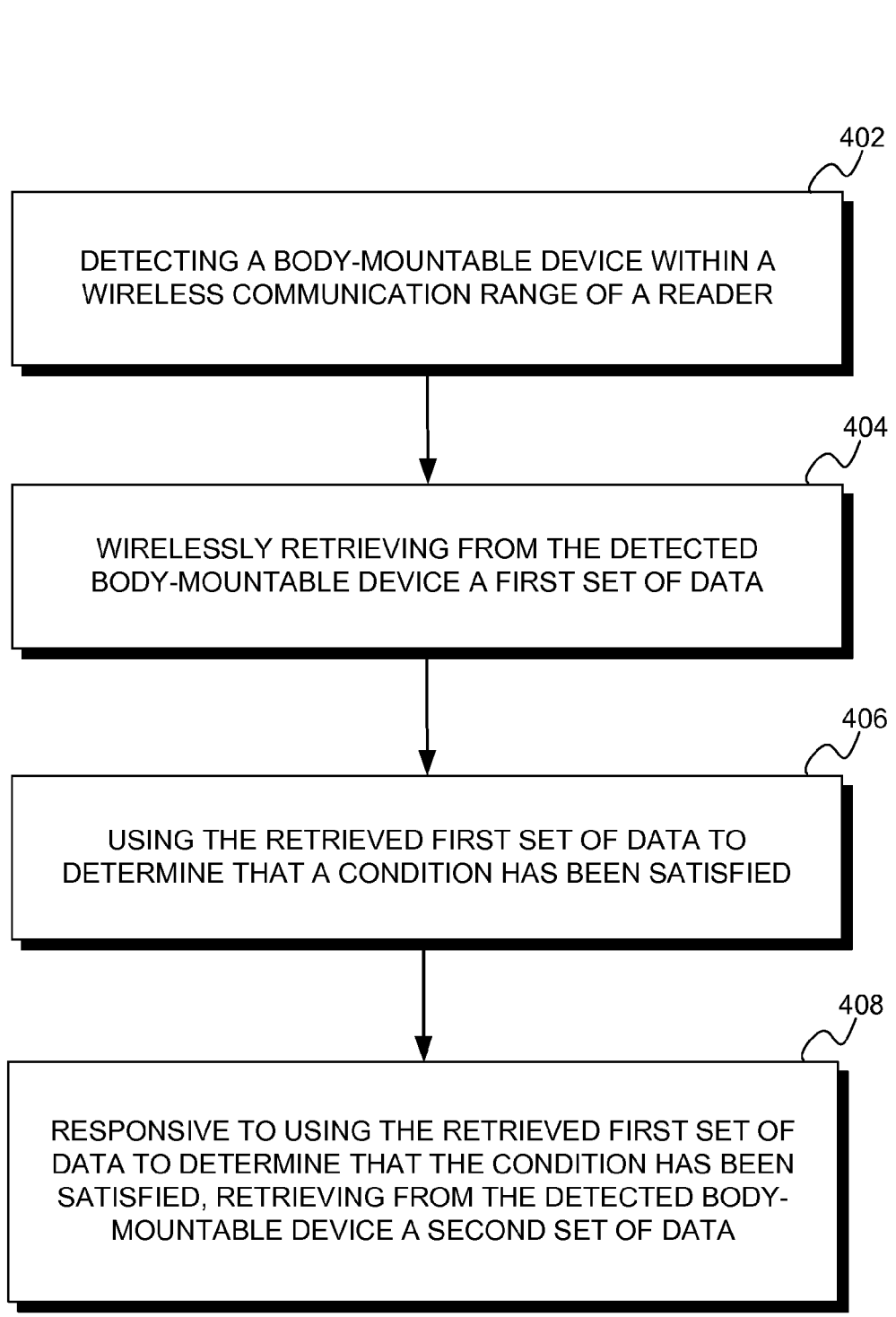
FIG. 4 is a block diagram of an example method.

FIG. 4 is a block diagram of an example method 400 for operating a reader in accordance with at least some embodiments described herein. Method 400 could be used in connection with the devices 110, 190, and/or 210 for example. Method 400 may include one or more operations, functions, or actions as illustrated by one or more of blocks 402-406. Although the blocks are illustrated in a sequential order, these blocks may in some instances be performed in parallel, and/or in a different order than those described herein. Also, the various blocks may be combined into fewer blocks, divided into additional blocks, and/or removed based upon the desired implementation.

In addition, for the method 400 and other processes and methods disclosed herein, the flowchart shows functionality and operation of one possible implementation of present embodiments. In this regard, each block may represent a module, a segment, or a portion of a manufacturing or operation process.

At block 402, the method 400 may involve detecting a body-mountable device within a wireless communication range of a reader. For instance, this may involve the external reader 190 detecting that the body-mountable device 110 is within a wireless communication range of the external reader 190. As described above, the body-mountable device may take a variety of forms. For instance, the body-mountable device may take the form of an eye-mountable device that includes a transparent material having a concave mounting surface configured to be removably mounted on a corneal surface. The transparent material may further include a surface opposite the mounting surface, wherein the surface opposite the mounting surface includes a convex surface configured to be compatible with eyelid motion when the concave surface is mounted on the corneal surface.

At block 404, the method may involve wirelessly retrieving from the detected body-mountable device a first set of data. For instance, this may involve the external reader 190 wirelessly retrieving from the detected body-mountable device 110 a first set of data. The first set of data may take a variety of forms. For example, the first set of data may include power-related data. For instance, where the body-mountable device includes a battery, the first set of data may include an indication of an amount of energy stored in the battery. Additionally or alternatively, where the body-mountable device includes a photovoltaic cell, the first set of data may include an indication of an amount of every available from the photovoltaic cell. The first set of data may also include obtained sensor metadata (i.e., data about obtained sensor data). For instance, the first set of data may include an indication of an amount of obtained sensor data stored in the body-mountable device. Other types of data are possible as well.

In some examples, the body-mountable device can transmit the obtained sensor data to the external reader via radio frequency radiation (RF radiation) and/or via via light modulation as described above.

At block 406, the method may involve using the retrieved first set of data to determine that a condition has been satisfied. For instance, this may involve the external reader 190 using the retrieved first set of data to determine that a condition has been satisfied. The condition may take a variety of forms. For example, the condition may be a condition that the body-mountable device is storing a threshold amount of energy. As another example, the condition may be a condition that the body-mountable device is not storing a threshold amount of sensor data. In another example, the condition may include two or more subparts. For instance, the condition may be a condition that (i) the body-mountable device is storing a threshold amount of energy, and (ii) the body-mountable device is not storing a threshold amount of sensor data. Other conditions are possible as well. Note that for a condition that uses a particular threshold, the threshold may vary to suit a desired configuration.

At block 408, the method may involve responsive to using the retrieved first set of data to determine that the condition has been satisfied, retrieving from the detected body-mountable device a second set of data. For instance, this may involve responsive to the external reader 190 using the retrieved first set of data to determine that the condition has been satisfied, the external reader 190 retrieving from the detected body-mountable device 110 a second set of data. The second set of data may take a variety of forms. For example, the second set of data may include obtained sensor data stored in the body-mountable device.

Figure 5:
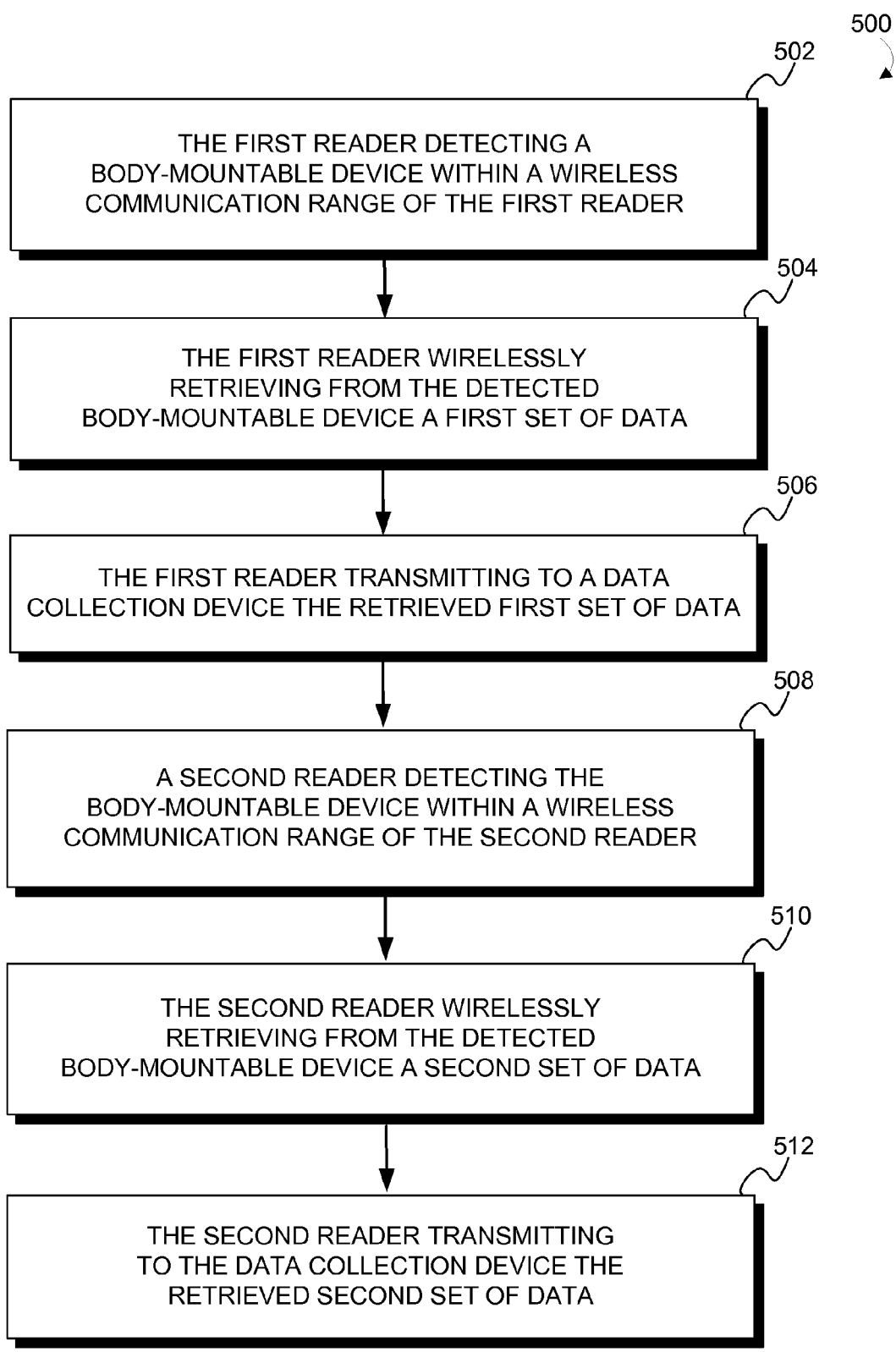
FIG. 5 is a block diagram of another example method.

FIG. 5 is a block diagram of an example method 500 for operating a reader 190, in accordance with at least some embodiments described herein. Method 500 could be used with the devices 110, 112, 190, and/or 210 for example. Method 500 may include one or more operations, functions, or actions as illustrated by one or more of blocks 502-506. Although the blocks are illustrated in a sequential order, these blocks may in some instances be performed in parallel, and/or in a different order than those described herein. Also, the various blocks may be combined into fewer blocks, divided into additional blocks, and/or removed based upon the desired implementation.

At block 502, the method 500 may involve a first reader detecting a body-mountable device within a wireless communication range of the first reader. For instance, this may involve the external reader 190a detecting that the body-mountable device 110 is within a wireless communication range of the external reader 190a. As described above, the body-mountable device may take a variety of forms. For instance, the body-mountable device may take the form of an eye-mountable device that includes a transparent material having a concave mounting surface configured to be removably mounted on a corneal surface. The transparent material may further include a surface opposite the mounting surface, wherein the surface opposite the mounting surface includes a convex surface configured to be compatible with eyelid motion when the concave surface is mounted on the corneal surface.

At block 504, the method may involve the first reader wirelessly retrieving from the detected body-mountable device a first set of data. For instance, this may involve the external reader 190a wirelessly retrieving from the detected body-mountable device 110 a first set of data.

At block 506, the method may involve the first reader transmitting to a data collection device the retrieved first set of data. For instance, this may involve the external reader 190a transmitting to the data collection device 302 the retrieved first set of data.

At block 508, the method may involve a second reader detecting the body-mountable device within a wireless communication range of the second reader. For instance, this may involve the second external reader 190b detecting that the body-mountable device 110 is within a wireless communication range of the external reader 190b.

At block 510, the method may involve the second reader wirelessly retrieving from the detected body-mountable device a second set of data. For instance, this may involve the external reader 190b wirelessly retrieving from the detected body-mountable device 110 a second set of data.

At block 512, the method may involve the second reader transmitting to the data collection device the retrieved second set of data. For instance, this may involve the external reader 190*b* transmitting to the data collection device 302 the retrieved second set of data.

Figure 6:
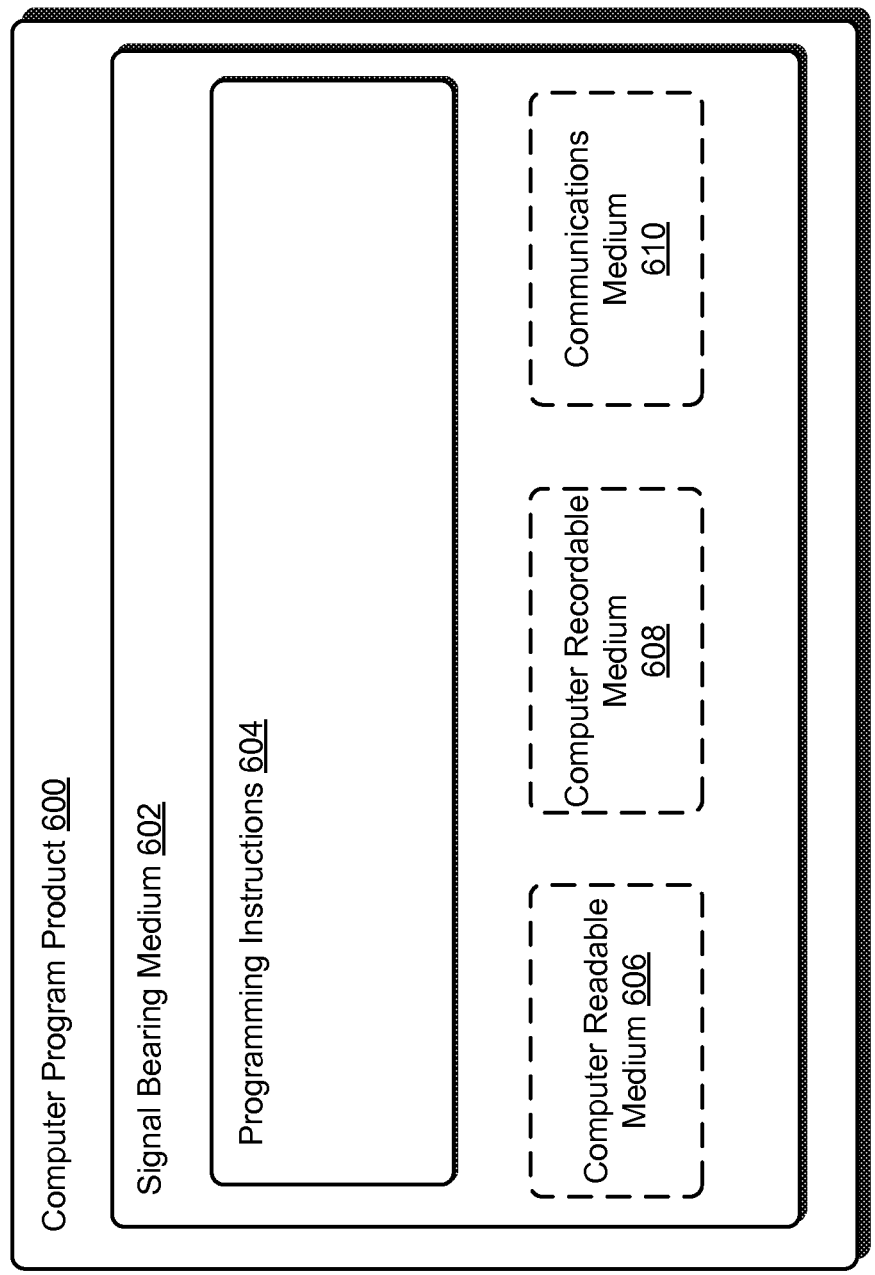
FIG. 6 is a block diagram of an example computer-readable medium.

FIG. 6 depicts an example computer-readable medium configured according to at least some embodiments described herein. In example embodiments, the example system can include one or more processors, one or more forms of memory, one or more input devices/interfaces, one or more output devices/interfaces, and machine readable instructions that when executed by the one or more processors cause the system to carry out the various functions tasks, capabilities, etc., described above.

As noted above, in some embodiments, the disclosed techniques (e.g. methods 400 and 500) can be implemented by computer program instructions encoded on a non-transitory computer readable storage media in a machine-readable format, or on other non-transitory media or articles of manufacture. FIG. 6 is a schematic illustrating a conceptual partial view of an example computer program product that includes a computer program for executing a computer process on a computing device, arranged according to at least some embodiments disclosed herein.

In one embodiment, the example computer program product 600 is provided using a signal bearing medium 602. The signal bearing medium 602 may include one or more programming instructions 604 that, when executed by one or more processors may provide functionality or portions of the functionality described above with respect to FIGS. 1-5. In some examples, the signal bearing medium 602 can be a non-transitory computer-readable medium 606, such as, but not limited to, a hard disk drive, a Compact Disc (CD), a Digital Video Disk (DVD), a digital tape, memory, etc. In some implementations, the signal bearing medium 602 can be a computer recordable medium 608, such as, but not limited to, memory, read/write (R/W) CDs, R/W DVDs, etc. In some implementations, the signal bearing medium 602 can be a communication medium 610 (e.g., a fiber optic cable, a waveguide, a wired communications link, a wireless communication link, etc.). Thus, for example, the signal bearing medium 602 can be conveyed by a wireless form of the communications medium 610.

The one or more programming instructions 604 can be, for example, computer executable and/or logic implemented instructions. In some examples, a computing device such as the processor-equipped external reader 190 of FIG. 1 is configured to provide various operations, functions, or actions in response to the programming instructions 604 conveyed to the computing device by one or more of the computer readable medium 606, the computer recordable medium 608, and/or the communications medium 610.

The non-transitory computer readable medium 606 can also be distributed among multiple data storage elements, which could be remotely located from each other. The computing device that executes some or all of the stored instructions could be an external reader such as the external reader 190 illustrated in FIG. 1, or another mobile computing platform, such as a smartphone, tablet device, personal computer, head-mounted device, etc. Alternatively, the computing device that executes some or all of the stored instructions could be remotely located computer system, such as a server. For example, the computer program product 600 can implement the functionalities discussed in the description of FIGS. 1-5.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

Where example embodiments involve information related to a person or a device of a person, some embodiments may include privacy controls. Such privacy controls may include, at least, anonymization—of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location) and an opportunity to control whether or how personal information is used. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and how the collected information is used.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

What is claimed is:

1. A method comprising:
   a reader detecting a body-mountable device within a wireless communication range of the reader, wherein the body-mountable device comprises a sensor configured to obtain sensor data and a data storage configured to store the obtained sensor data;
   the reader wirelessly retrieving from the detected body-mountable device a first set of data;
   the reader determining using the retrieved first set of data that the body-mountable device is able to transmit the obtained sensor data to the reader in a single communication session; and
   responsive to determining using the retrieved first set of data that the body-mountable device is able to transmit the obtained sensor data to the reader in a single communication session, the reader retrieving from the detected body-mountable device a second set of data, wherein the second set of data comprises the obtained sensor data.

2. The method of claim 1, wherein the first set of data comprises an indication of an amount of energy stored in the body-mountable device.

3. The method of claim 1, wherein the body-mountable device comprises a battery, and wherein the first set of data comprises an indication of an amount of energy stored in the battery.

4. The method of claim 1, wherein the body-mountable device comprises a photovoltaic cell, and wherein the first set of data comprises an indication of an amount of energy available from the photovoltaic cell.

5. The method of claim 1, wherein the first set of data comprises an indication of an amount of the obtained sensor data.

6. The method of claim 4, wherein the obtained sensor data comprises data indicative of an analyte concentration.

7. The method of claim 1, wherein the reader determining using the retrieved first set of data that the body-mountable device is able to transmit the obtained sensor data to the reader in a single communication session comprises the reader determining that the body-mountable device is storing a threshold amount of energy.

8. The method of claim 1, wherein the reader determining using the retrieved first set of data that the body-mountable device is able to transmit the obtained sensor data to the reader in a single communication session comprises the reader determining that the body-mountable device is not storing a threshold amount of sensor data.

9. The method of claim 1, wherein the reader determining using the retrieved first set of data that the body-mountable device is able to transmit the obtained sensor data to the reader in a single communication session comprises the reader determining that (i) the body-mountable device is storing a threshold amount of energy, and (ii) the body-mountable device is not storing a threshold amount of sensor data.

10. A reader comprising
a wireless communication interface;
a processor; and
a computer-readable medium including instructions that, when executed by the processor, cause the reader to perform a set of functions comprising:
    detecting a body-mountable device within a wireless communication range of the reader, wherein the body-mountable device comprises a sensor configured to obtain sensor data and a data storage configured to store the obtained sensor data;
    wirelessly retrieving, using the wireless communication interface, from the detected body-mountable device a first set of data;
    determining using the retrieved first set of data that the body-mountable device is able to transmit the obtained sensor data to the reader in a single communication session; and
    responsive to determining using the retrieved first set of data that the body-mountable device is able to transmit the obtained sensor data to the reader in a single communication session, retrieving, using the wireless communication interface, from the detected body-mountable device a second set of data, wherein the second set of data comprises the obtained sensor data.

11. The reader of claim 10, wherein the first set of data comprises an indication of an amount of energy stored in the body-mountable device.

12. The reader of claim 10, wherein the first set of data comprises an indication of an amount of the obtained sensor data.

13. The reader of claim 12, wherein the obtained sensor data comprises data indicative of an analyte concentration.

14. The reader of claim 10, wherein determining using the retrieved first set of data that the body-mountable device is able to transmit the obtained sensor data to the reader in a single communication session comprises determining that the body-mountable device is storing a threshold amount of energy.

15. The reader of claim 10, wherein determining using the retrieved first set of data that the body-mountable device is able to transmit the obtained sensor data to the reader in a single communication session comprises determining that the body-mountable device is not storing a threshold amount of sensor data.

16. A method comprising:
a first reader detecting a body-mountable device within a wireless communication range of the first reader, wherein the body-mountable device comprises a sensor configured to obtain sensor data indicative of an analyte concentration and a data storage configured to store the obtained sensor data;
the first reader wirelessly retrieving from the detected body-mountable device a first portion of the obtained sensor data;
the first reader transmitting to a data collection device the retrieved first portion of the obtained sensor data;
a second reader detecting the body-mountable device within a wireless communication range of the second reader;
the second reader wirelessly retrieving from the detected body-mountable device a second portion of the obtained sensor data; and
the second reader transmitting to the data collection device the retrieved second portion of the obtained sensor data.

17. The method of claim 1, wherein the reader detecting the body-mountable device comprises:
the reader transmitting a query message to the body-mountable device; and
the reader receiving an acknowledgement message from the body-mountable device.

18. The reader of claim 10, wherein detecting the body-mountable device comprises:
the reader transmitting a query message to the body-mountable device; and
the reader receiving an acknowledgement message from the body-mountable device.

19. The method of claim 16, wherein each of the first and second readers detects the body-mountable device by transmitting a respective query message to the body-mountable device and receiving a respective acknowledgement message from the body-mountable device.

* * * * *